(12) United States Patent
Palushi et al.

(10) Patent No.: US 11,033,721 B2
(45) Date of Patent: Jun. 15, 2021

(54) GUIDEWIRE FOR DILATING EUSTACHIAN TUBE VIA MIDDLE EAR

(71) Applicant: Acclarent, Inc., Irvine, CA (US)

(72) Inventors: Jetmir Palushi, Irvine, CA (US); Fatemeh Akbarian, Rancho Palos Verdes, CA (US); Itzhak Fang, Irvine, CA (US); Athanasios Papadakis, Newport Beach, CA (US)

(73) Assignee: Acclarent, Inc., Irvine, CA (US)

( * ) Notice: Subject to any disclaimer, the term of this patent is extended or adjusted under 35 U.S.C. 154(b) by 290 days.

(21) Appl. No.: 16/015,293

(22) Filed: Jun. 22, 2018

(65) Prior Publication Data
US 2019/0388661 A1      Dec. 26, 2019

(51) Int. Cl.
*A61M 29/02* (2006.01)
*A61B 34/20* (2016.01)
*A61M 25/09* (2006.01)

(52) U.S. Cl.
CPC ............. *A61M 29/02* (2013.01); *A61B 34/20* (2016.02); *A61M 25/09* (2013.01); *A61B 2034/2051* (2016.02); *A61M 2025/09116* (2013.01); *A61M 2025/09183* (2013.01); *A61M 2210/0675* (2013.01)

(58) Field of Classification Search
CPC ...... A61F 11/00; A61F 11/002; A61F 11/004; A61M 2025/09008; A61M 2210/0675; A61M 29/02; A61M 2029/025; A61M 25/09; A61M 25/10; A61M 2025/09175; A61M 2025/09183; A61B 34/20; A61B 2034/2046; A61B 2034/2051
See application file for complete search history.

(56) References Cited

U.S. PATENT DOCUMENTS

| 4,946,466 | A | * | 8/1990 | Pinchuk ................. A61M 25/09 604/913 |
| 5,167,239 | A | * | 12/1992 | Cohen .............. A61B 17/22032 600/434 |
| 6,104,944 | A | * | 8/2000 | Martinelli ................. A61B 5/06 128/899 |
| 6,228,072 | B1 | | 5/2001 | Omaleki et al. |
| 7,720,521 | B2 | | 5/2010 | Chang et al. |
| 10,165,928 | B2 | * | 1/2019 | Hunter ............... A61B 1/00094 |
| 2003/0088263 | A1 | | 5/2003 | Bonnette et al. |
| 2006/0200191 | A1 | | 9/2006 | Zadno-Azizi |

(Continued)

OTHER PUBLICATIONS

International Search Report and Written Opinion dated Dec. 5, 2019 for International Application No. PCT/IB2019/055092, 14 pages.

(Continued)

*Primary Examiner* — Robert A Lynch
(74) *Attorney, Agent, or Firm* — Frost Brown Todd LLC

(57) ABSTRACT

A guidewire includes a guidewire shaft and an inflatable element arranged at a distal end of the guidewire shaft. At least a portion of the guidewire shaft is formed of metal, and the guidewire shaft includes a lumen that fluidly communicates with an interior of the inflatable element. The inflatable element is operable to transition between a deflated state in which the inflatable element is configured to pass through an isthmus of a Eustachian tube (ET), and an inflated state in which the inflatable element is configured to dilate the ET.

20 Claims, 12 Drawing Sheets

(56) References Cited

U.S. PATENT DOCUMENTS

| | | | |
|---|---|---|---|
| 2008/0255446 A1* | 10/2008 | Akins | A61B 5/6851 |
| | | | 600/424 |
| 2009/0163890 A1* | 6/2009 | Clifford | A61B 8/12 |
| | | | 604/514 |
| 2010/0274085 A1* | 10/2010 | Mugan | A61M 25/09 |
| | | | 600/115 |
| 2010/0274188 A1 | 10/2010 | Chang et al. | |
| 2013/0274715 A1 | 10/2013 | Chan et al. | |
| 2014/0364725 A1 | 12/2014 | Makower | |
| 2015/0374963 A1 | 12/2015 | Chan et al. | |
| 2016/0008083 A1 | 1/2016 | Kesten et al. | |
| 2016/0038719 A1* | 2/2016 | Asmus | A61M 25/09 |
| | | | 600/585 |
| 2016/0310042 A1 | 10/2016 | Kesten et al. | |
| 2017/0119583 A1 | 5/2017 | Chan et al. | |

OTHER PUBLICATIONS

U.S. Appl. No. 15/840,346, entitled "Dilation Instrument with Proximally Located Force Sensor," filed Dec. 13, 2017.

U.S. Appl. No. 15/933,737, entitled "Apparatus to Secure Field Generating Device to Chair," filed Mar. 23, 2018.

* cited by examiner

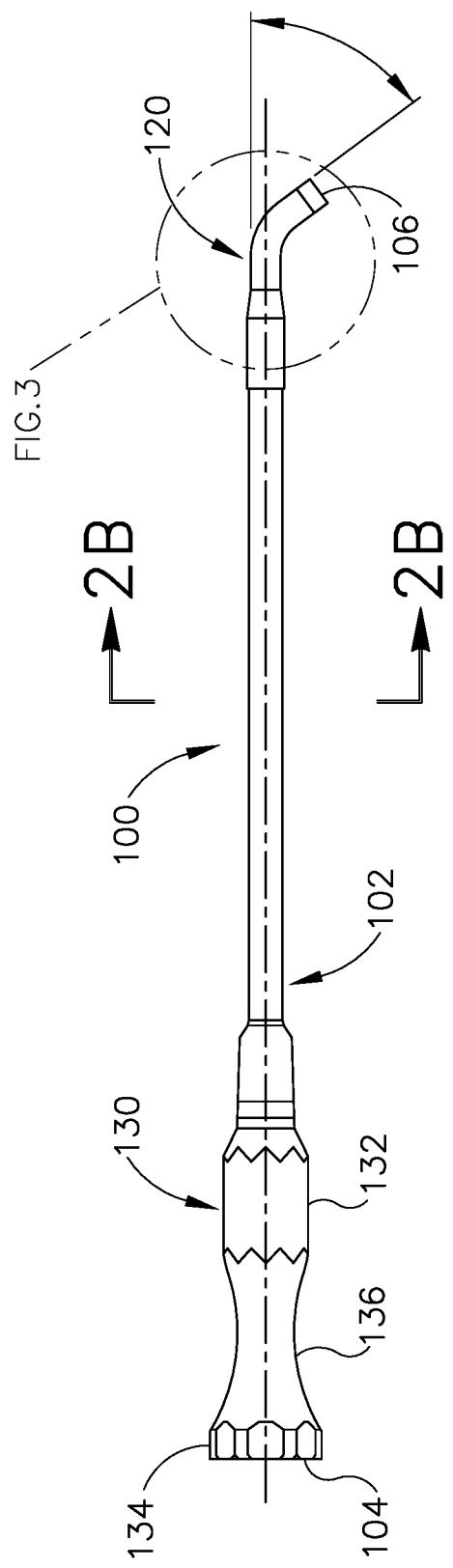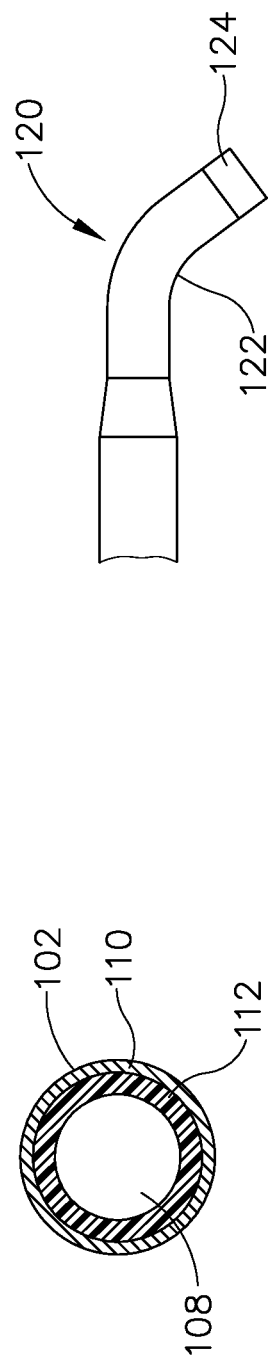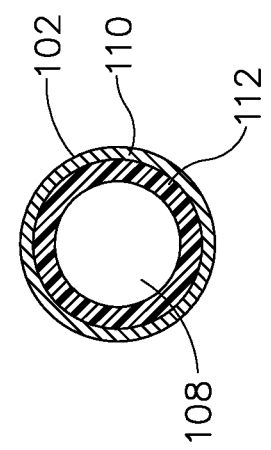

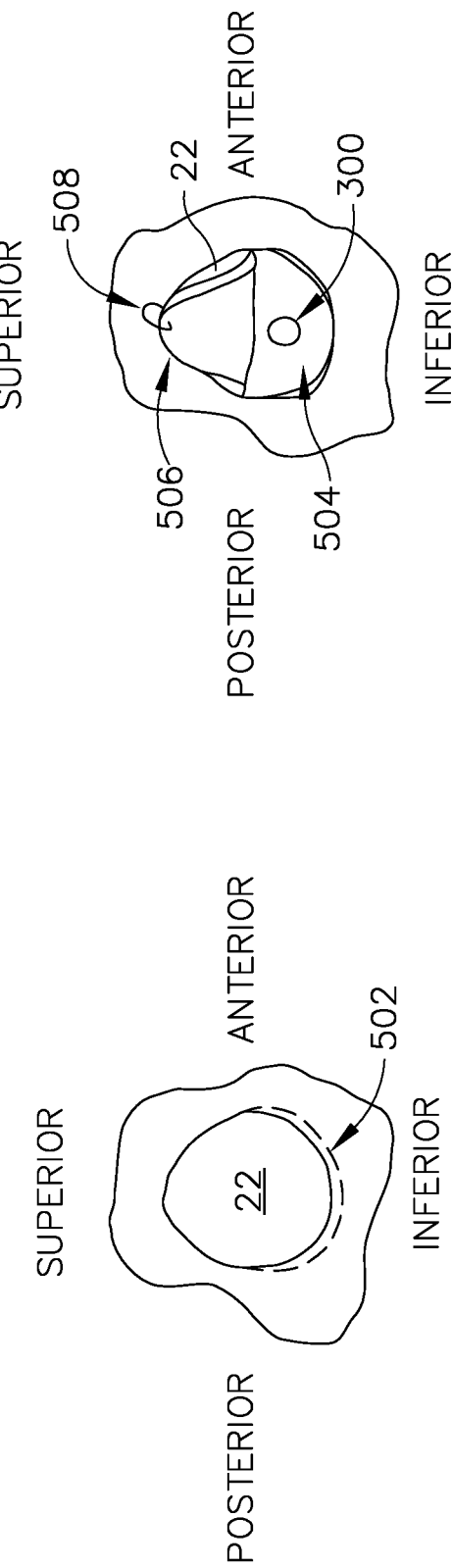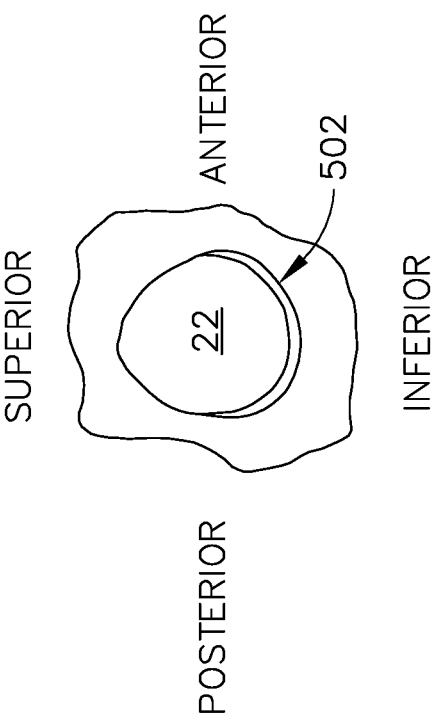

GUIDEWIRE FOR DILATING EUSTACHIAN TUBE VIA MIDDLE EAR

BACKGROUND

As shown in FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup).

The ET (26) is a narrow channel connecting the middle ear (14) with the nasopharynx (30). The ET (26) functions as a pressure equalizing valve for the middle ear (14), which is normally filled with air. When functioning properly, the ET (26) opens for a fraction of a second periodically in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms. Obstruction or blockage of the ET (26) results in a negative middle ear (14) pressure, with retraction (sucking in) of the eardrum (22). This may be accompanied by some ear discomfort, such as a fullness or pressure feeling, and may result in a mild hearing impairment and head noise (tinnitus). If the obstruction is prolonged, the middle ear (14) may eventually become infected.

Methods for treating the middle ear (14) and the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Patent Pub. No. 2015/0374963, entitled "Vent Cap for a Eustachian Tube Dilation System," published on Dec. 31, 2015, issued as U.S. Pat. No. 10,350,396 on Jul. 16, 2019, the disclosure of which is incorporated by reference herein. As described in those references, functioning of the ET (26) may be improved by dilating the ET (26) with an expandable dilator instrument.

While a variety of surgical instruments have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2A depicts a side elevational view of an exemplary guide catheter;

FIG. 2B depicts a cross-sectional view of the guide catheter of FIG. 2A, taken along line 2B-2B in FIG. 2A;

FIG. 3 depicts an enlarged elevational view of the distal end of the guide catheter of FIG. 2A;

FIG. 12A depicts a schematic view of a tympanic membrane of the patient of FIG. 11A, viewing medially from the ear canal, before the step shown in FIG. 11A;

FIG. 12B depicts a schematic view of the tympanic membrane of FIG. 12A, showing tissue surrounding the tympanic membrane having been incised and the tympanic membrane having been folded upwardly to provide access to the middle ear, with the guidewire of FIG. 7 having been inserted into the middle ear to perform the steps shown in FIGS. 11A-11B; and FIG. 12C depicts a schematic view of the tympanic membrane of FIG. 12A, showing the tympanic membrane and surrounding tissue replaced to their original positions using a fixation method, after completion of the steps shown in FIGS. 11A-11B.

Figure 1:
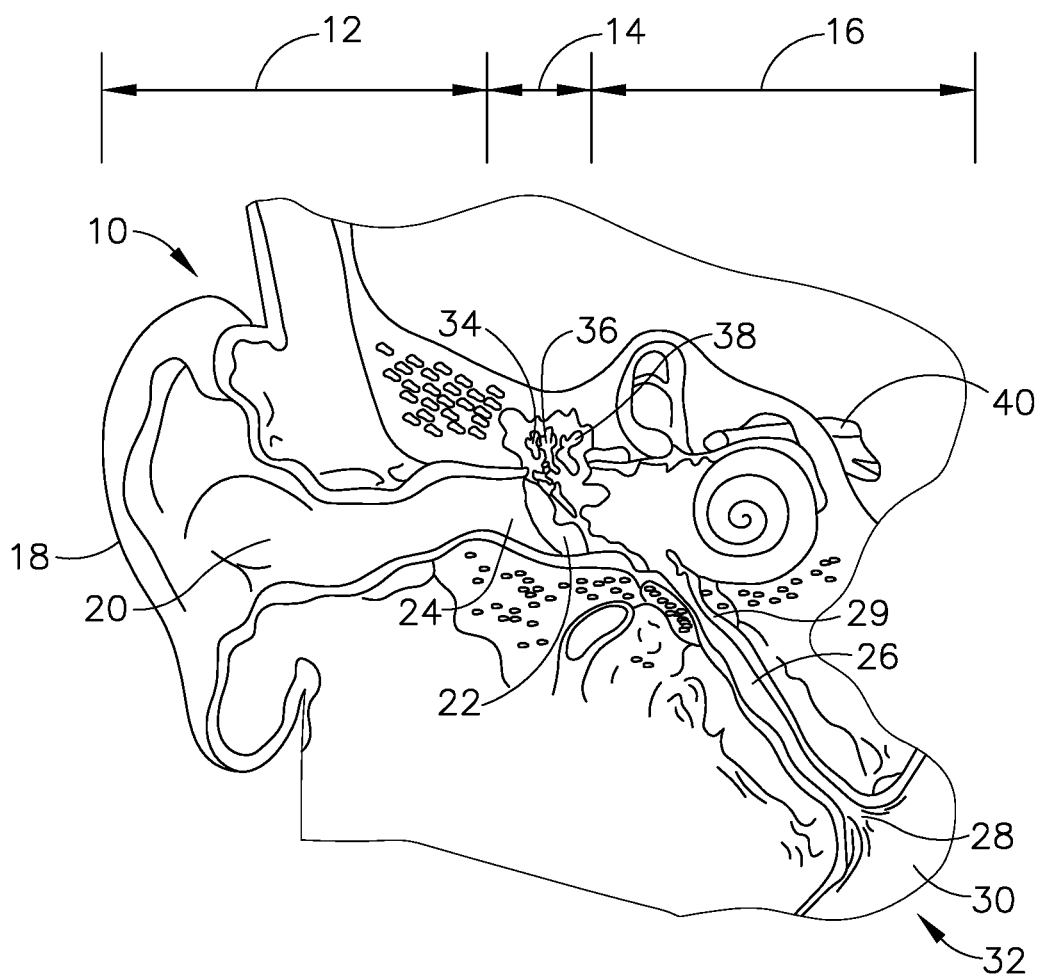
FIG. 1 depicts a cross-sectional view of a patient's head, showing the inner ear, the middle ear, the outer ear, and the Eustachian tube connecting the middle ear with the nasopharynx region of the throat.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Eustachian Tube Dilation Catheter System

One example of a treatment that may be performed to treat an ET (26) that does not provide sufficient communication between the middle ear (14) and the pharyngeal ostium (28) includes accessing and dilating the ET (26) using a guide catheter (100) and a balloon dilation catheter (200), examples of which are shown in FIGS. 2A-5. Guide catheter (100) of the present example includes an elongate tubular shaft (102) that has a proximal end (104), a distal end (106) and a lumen (108) therebetween. As shown in FIG. 2B, shaft (102) has an outer shaft tube (110), an inner shaft tube (112) and a lumen (108). As shown in FIG. 3, the distal portion (120) of the guide catheter (100) has a bend (122) that facilitates access into the ET (26) via the pharyngeal ostium (28). The distal tip (124) of the distal portion (120) of the guide catheter (100) provides for atraumatic access to the ET (26). As shown in FIG. 2A, the proximal portion (130) of guide catheter (100) includes a proximal hub (132) to aid in insertion of balloon catheter (200) into the ET (26). The hub (132) has a larger diameter proximal end (134) and a smaller diameter middle section (136).

Figure 4A:
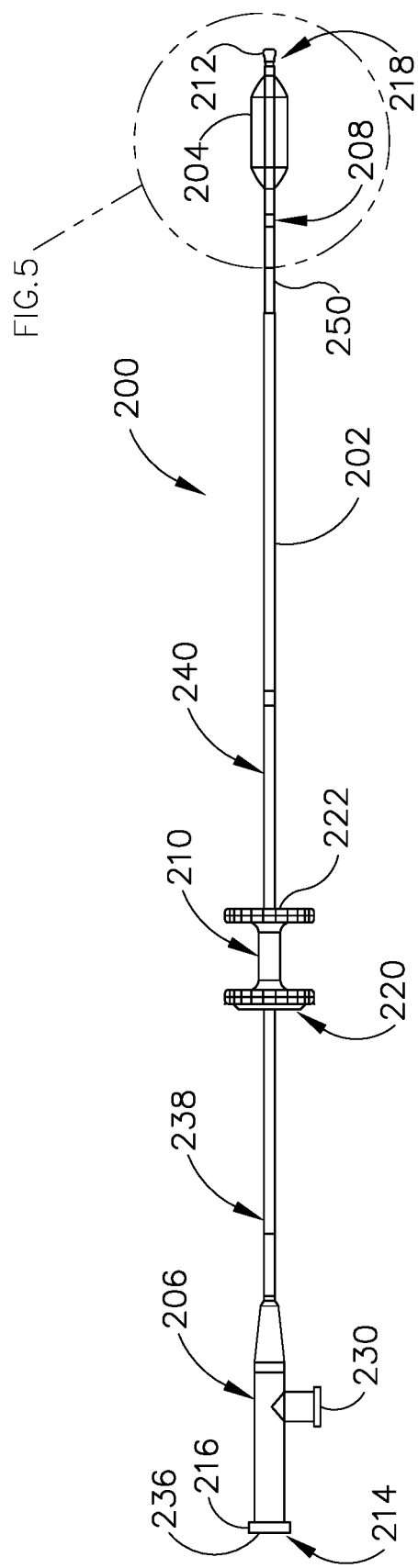
FIG. 4A depicts a side elevational view of an exemplary balloon dilation catheter that may be used with the guide catheter of FIG. 2A.
Figure 4B:
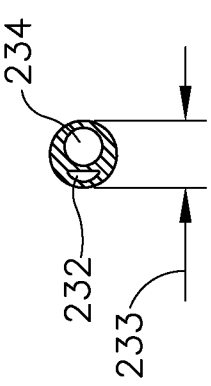
FIG. 4B depicts a cross-sectional view of the balloon dilation catheter of FIG. 4A, taken along line 4B-4B in FIG. 5.
Figure 5:
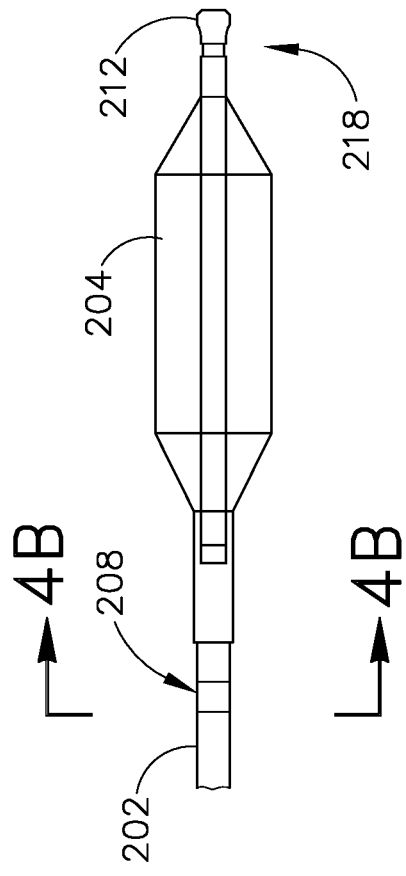
FIG. 5 depicts an enlarged elevational view of the distal end of the balloon dilation catheter of FIG. 4A.

As shown in FIG. 4A, balloon dilation catheter (200) of the present example generally includes an elongate shaft (202) having a proximal end (214) and a distal end (218). Balloon dilation catheter (200) further includes a balloon (204) longitudinally fixed at the distal end (218) of the elongate shaft (202). In some versions, the balloon (204) comprises a suitable non-compliant material. The balloon dilation catheter (200) generally includes a proximally located connection (230) for inflating/activating the balloon (204) by communicating a pressurized medium (e.g., saline) to balloon (204).

Figure 6A:
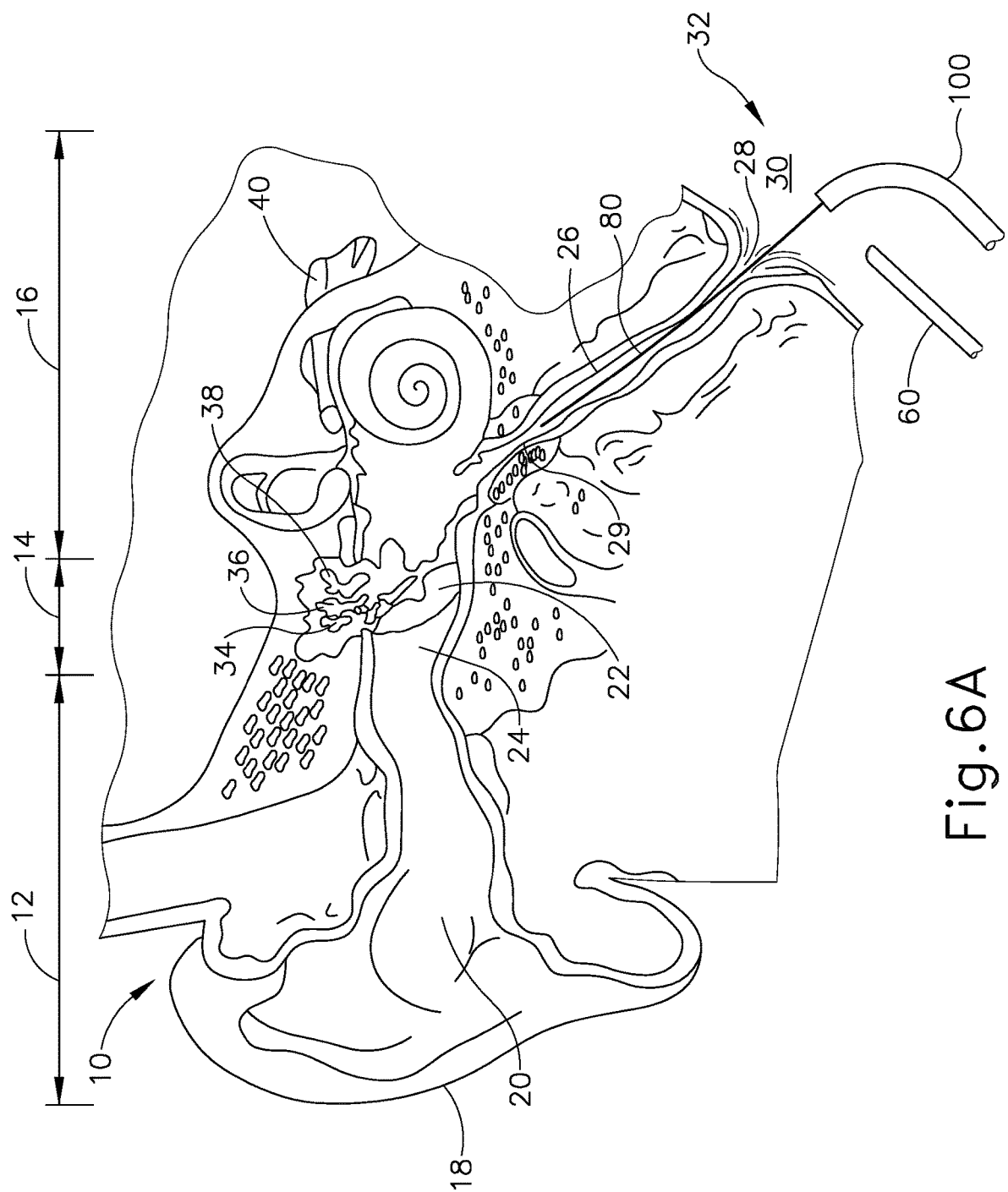
FIG. 6A depicts a cross-sectional view of a patient's head, showing the guide catheter of FIG. 2A, a guidewire, and an endoscope being positioned in relation to the patient's Eustachian tube via the throat.

Balloon (204) may be expanded to dilate the ET (26) after balloon (204) is placed in a desirable location in the ET (26). For example, dilation catheter (200) may be advanced to position the balloon (204) in the pharyngeal ostium (28) as shown in FIG. 6A. An endoscope (60) may be used to assist in positioning the dilation catheter (200). A marker (208) on a shaft of the dilation catheter (200) can be viewed from endoscope (60) to approximate a location of the balloon (204) relative to the opening of the ET (26) (e.g., pharyngeal ostium (28)) based on a distance of the marker (208) from a proximal end of the balloon (204).

Balloon dilation catheter (200) further includes an actuator (210). Actuator (210) has a proximal side (220) and a distal side (222). The portion (240) of elongate shaft (202) that is distal of actuator (210) is sufficiently stiff to be guided through the nasal cavity and into the ET (26). The portion (238) of elongate shaft (202) that is proximal of actuator (210) and the portion (250) that is distal to portion (240) is more flexible than the portion (240). The distal end (218) of balloon catheter (200) further includes a tip (212) and a flexible shaft portion (250) that extends from the distal end of the elongate shaft (202) to the proximal end of balloon (204). In the example shown in FIG. 4A, tip (212) is a bulbous polymeric blueberry-shaped, atraumatic tip.

Figure 6B:
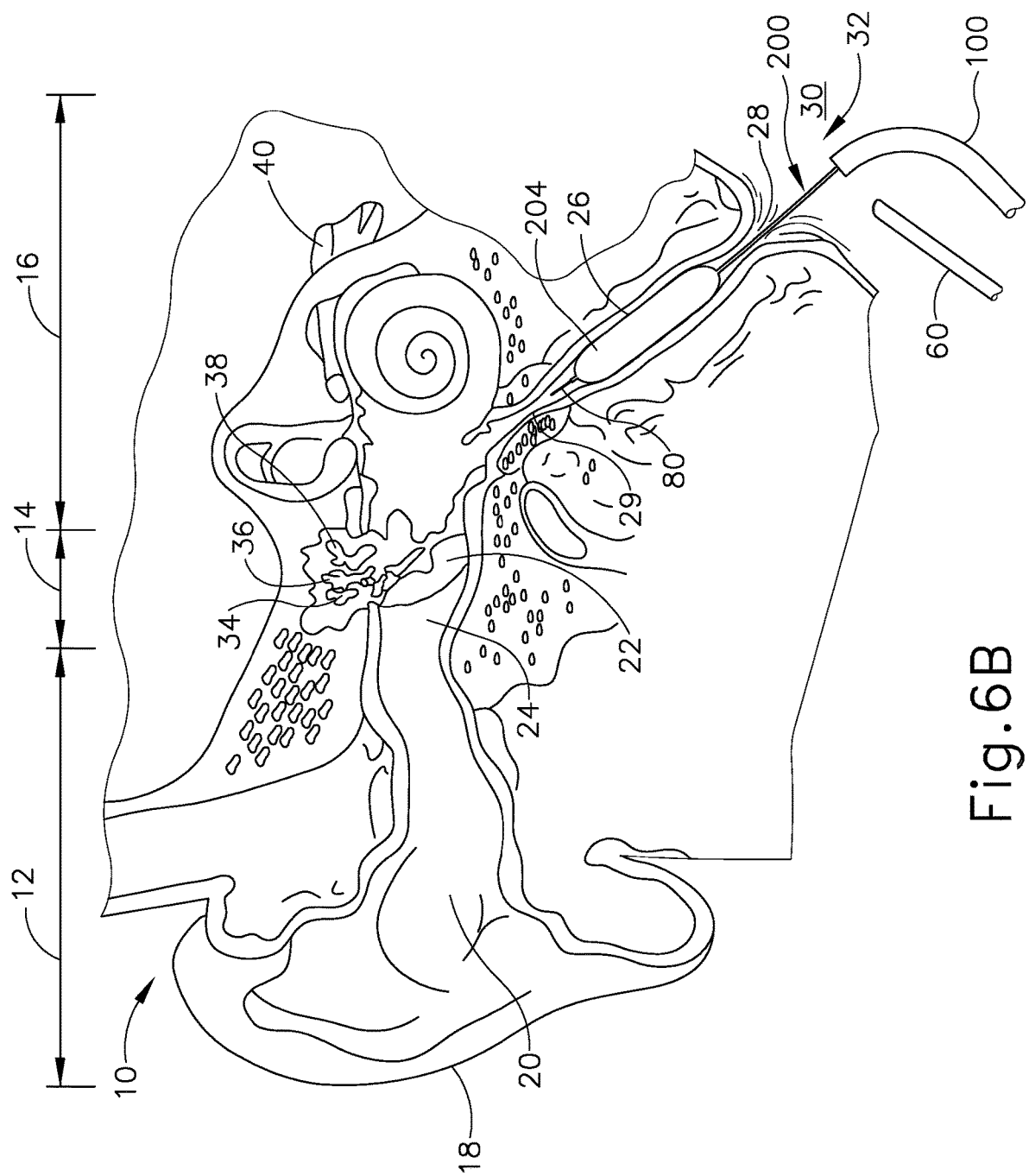
FIG. 6B depicts a cross-sectional view of the patient's head of FIG. 6A, showing the balloon dilation catheter of FIG. 4A inserted into the Eustachian tube and subsequently expanded to dilate the Eustachian tube.

After balloon (204) is positioned within the ET (26) and inflated to an expanded state (e.g., as shown in FIG. 6B), balloon (204) may be held in location while in an expanded state for an extended period of time (e.g. several seconds or minutes). The balloon catheter (200) may also deliver a substance to the ET (26), such as one or more of the therapeutic or diagnostic agents described herein. Balloon (204) may also carry an expandable stent for delivery into the ET (26) upon expansion of balloon (204). Balloon dilation catheter (200) and guide catheter (100) may be removed from the patient after balloon (204) has been deflated/unexpanded. The ET (26) will resume functioning, normally opening and closing to equalize atmospheric pressure in the middle ear (14) and protect the middle ear (14) from unwanted pressure fluctuations and loud sounds.

II. Exemplary Instrument for Dilating Eustachian Tube Via Middle Ear, and Related Surgical Navigation System In some instances, it may be difficult or impossible to access the ET (26) by inserting instruments through the nostril, into the oro-nasal cavity, and through the pharyngeal ostium, as shown in FIGS. 6A-6B described above. This may be due to the anatomical constraints of a patient or, in some instances, to the limitations of a particular practitioner's skill set. Therefore, in some instances, it may be more efficacious to access the ET (26) through the tympanic membrane (22) and the middle ear (14). However, due to the sensitive nature of the tympanic membrane (22) and middle ear structures, it may be advantageous to access the ET (26) in a manner that preserves the integrity of the ET (26) or minimizes trauma to the ET (26). Moreover, because this approach of accessing the ET (26) requires a practitioner to direct instruments through the isthmus (29), care must be taken due to the small size and sensitive nature of the isthmus (29) and adjacent structures of the inner ear (16).

The exemplary alternative dilation instrument (300) described below enables a practitioner to safely access the ET (26) via the middle ear (14) while still being operable to provide sufficient dilation of the ET (26) once positioned.

A. Exemplary Guidewire Having Inflatable Balloon

Figure 7:
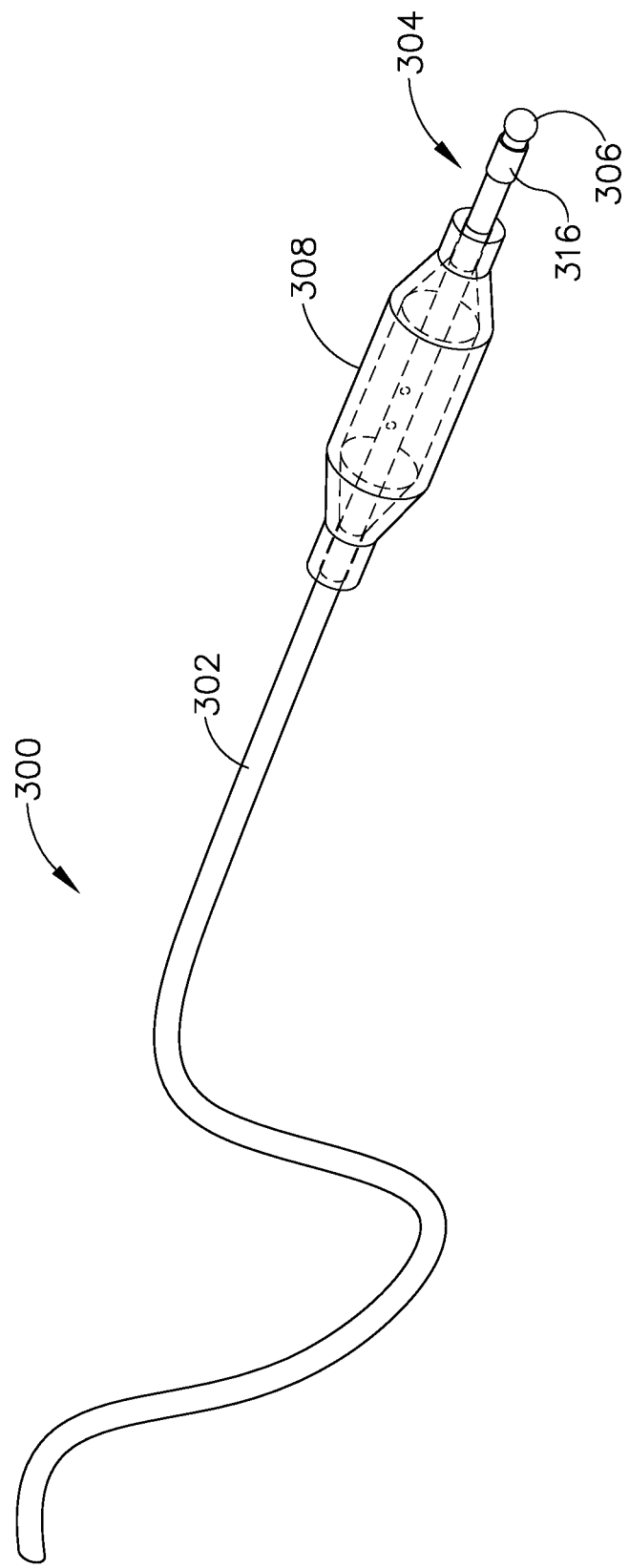
FIG. 7 depicts a perspective view of an exemplary guidewire having an inflatable balloon and a navigation sensor.

FIG. 7 shows an exemplary guidewire (300) that is sized and configured to access the ET (26) through the tympanic membrane (22), the middle ear (14), and the isthmus (29), and which may be used in place of guidewire (80) and balloon dilation catheter (200) described above. Guidewire (300) includes an elongate shaft (302) having a distal end (304), and a closed atraumatic tip (306) arranged at distal end (304). Atraumatic tip (306) of the present example is generally rounded in shape and is suitably sized to pass through the isthmus (29) and into the ET (26), as described in greater detail below.

Guidewire shaft (302) of the present example is suitably constructed with a lateral flexibility and a column strength (i.e., stiffness) sufficient to enable guidewire (300) to resiliently conform to the tortuous internal path extending between the middle ear (14) and the ET (26) of a patient without buckling or otherwise plastically deforming, and without an outer guidance device such as guide catheter (100). For instance, at least a portion of shaft (302) may be formed of braided stainless steel. In other examples, at least a portion of shaft (302) may be constructed with an outer coil and an inner core-wire. In various examples, guidewire shaft (302) may be formed of one or more metal materials such as 316 stainless steel, titanium, cobalt-chrome, nitinol, MP35N steel alloy, or various other suitable materials as disclosed in U.S. Pat. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein.

Figure 11A:
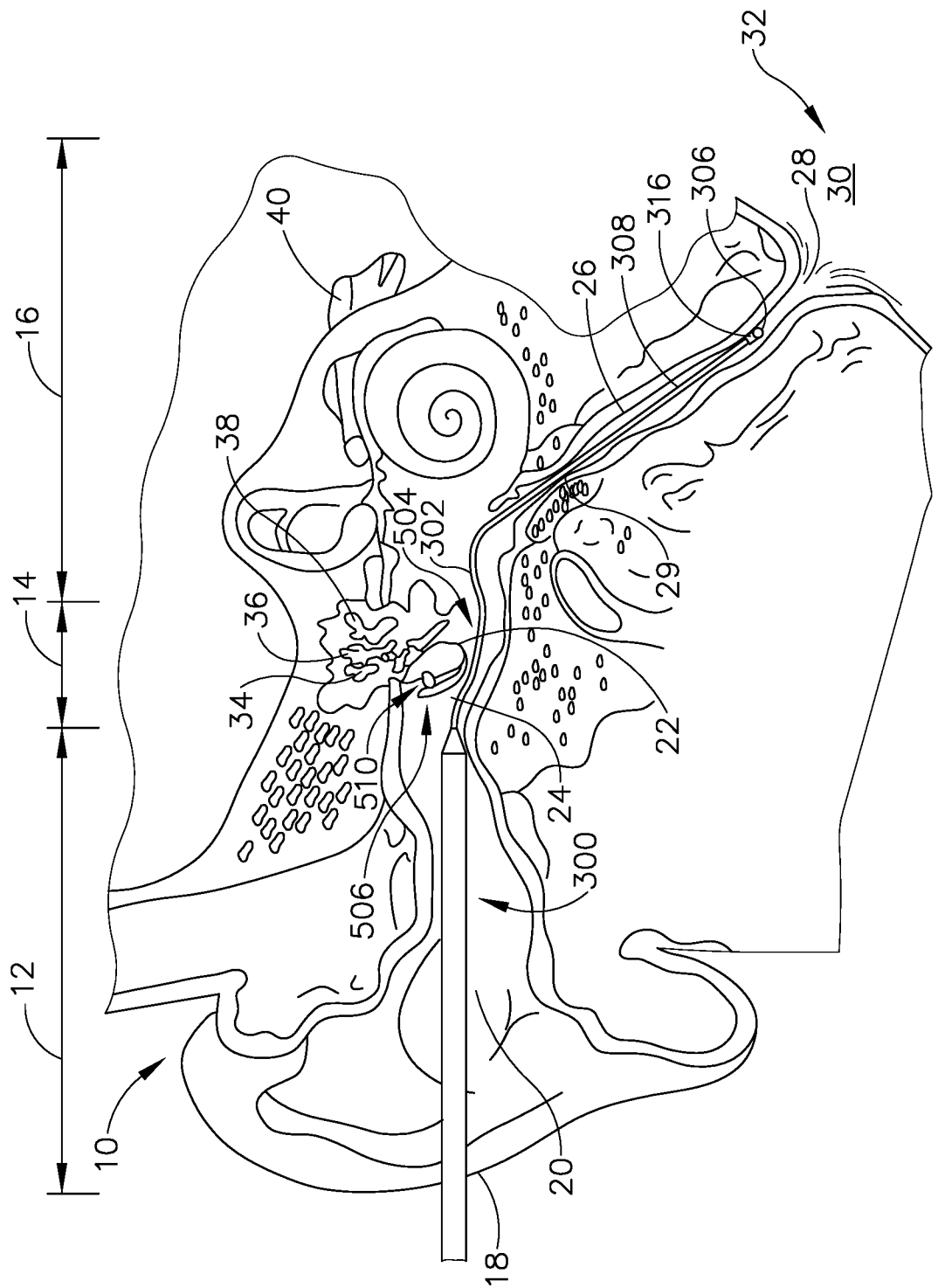
FIG. 11A depicts a cross-sectional view of a patient's head, showing a distal portion of the guidewire of FIG. 7 positioned within the patient's Eustachian tube via the middle ear.

Guidewire (300) of the present example further includes an expandable element in the form of an inflatable balloon (308) secured to an exterior of guidewire shaft (302) proximal to distal tip (306). Balloon (308) may be compliant, semi-compliant, or non-compliant in construction, and may be formed of any suitable polymeric material such as polyethylene terephthalate (PET), PEBAX® (polyether block amide), nylon, or the like. Balloon (308) of the present example is suitably sized and configured to provide guidewire (300) with a maximum outer diameter of less than or equal to approximately 1 millimeter when balloon (308) is deflated, as shown in FIG. 11A, and a maximum outer diameter of approximately 6 millimeters or greater when balloon (308) is fully inflated, as shown in FIGS. 7-9 and 11B. In at least some applications, a maximum outer diameter of approximately 6 millimeters provides sufficient dilation of a patient's ET (26) during an ET dilation procedure. It will be appreciated, however, that balloon (308) may be suitably configured to assume other maximum sizes for use in other applications and dilation procedures. Balloon (308) of the present example may have a working length of approximately 12 millimeters to approximately 24 millimeters. In other examples, balloon (308) may have a working length of approximately 20 millimeters to approximately 40 millimeters.

Figure 8:
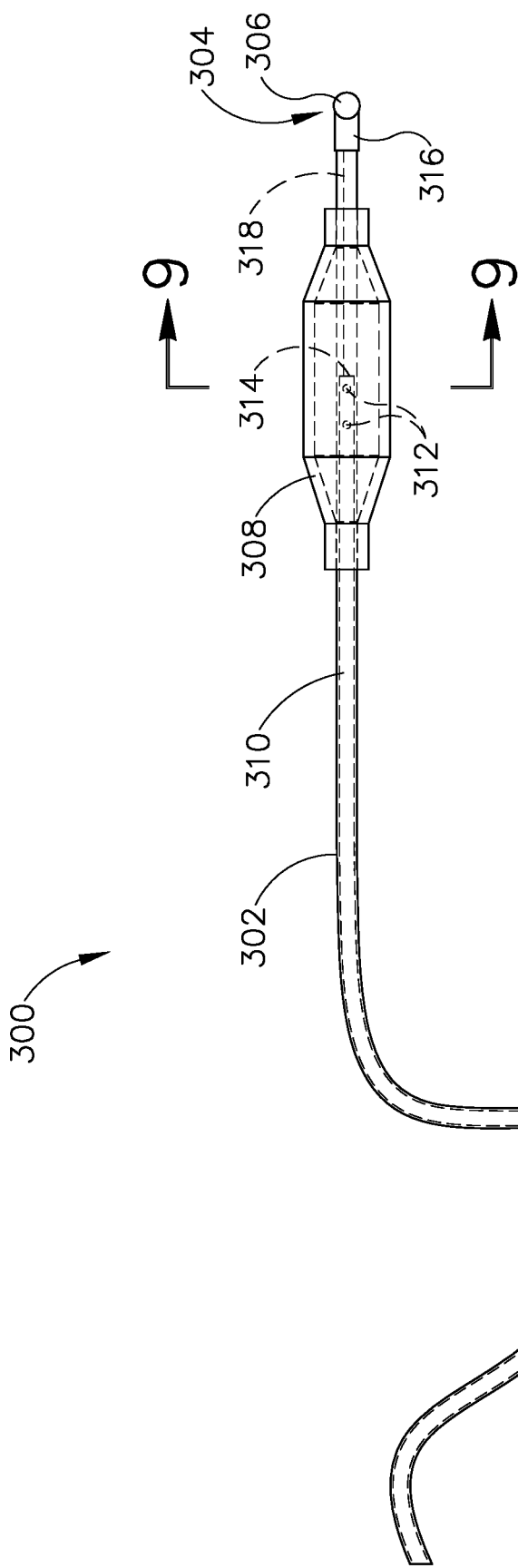
FIG. 8 depicts a side elevational view of the guidewire of FIG. 7, showing an internal inflation lumen and a sensor wire of the guidewire schematically.
Figure 9:
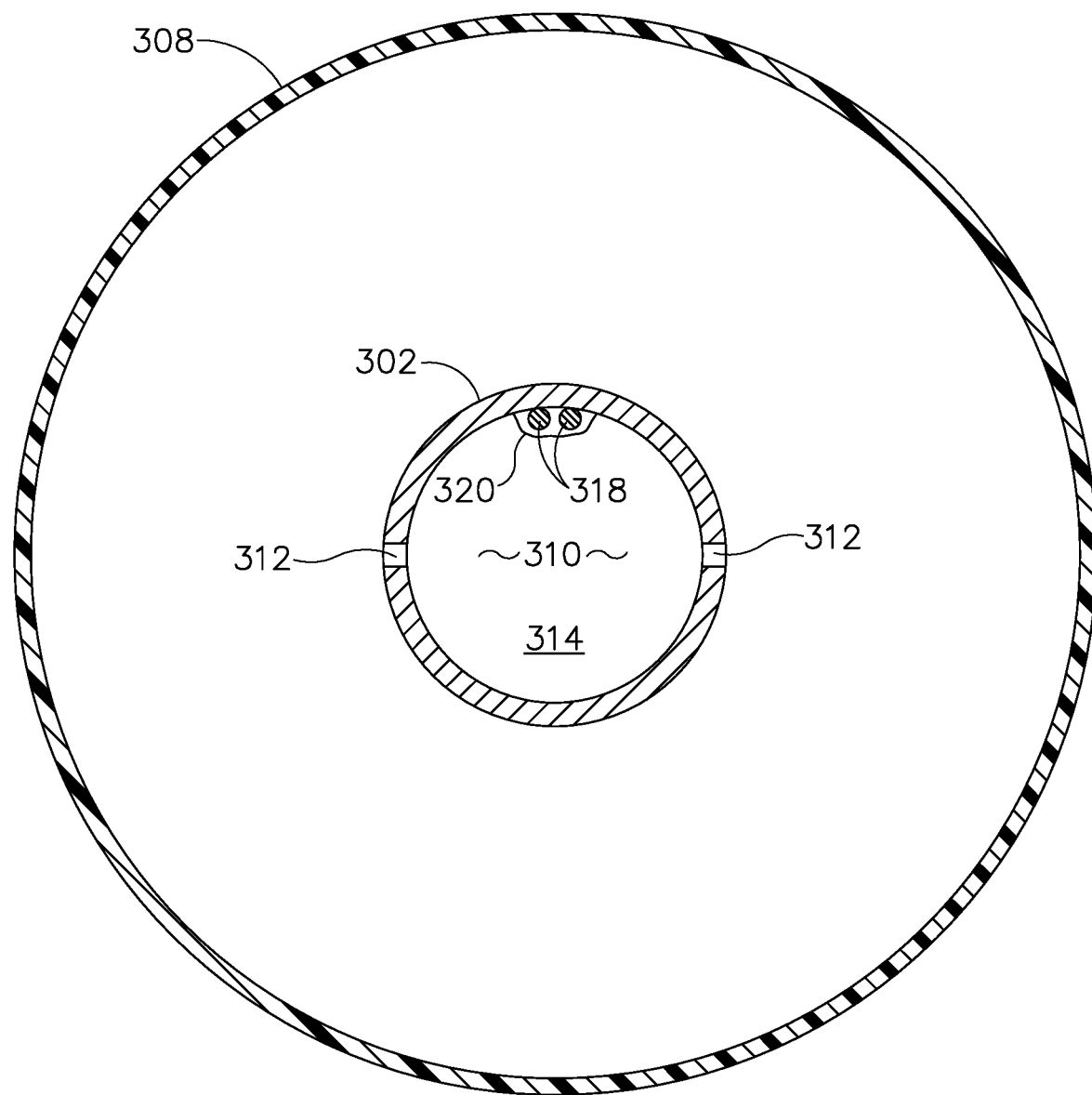
FIG. 9 depicts a cross-sectional view of the guidewire of FIG. 7, taken along line 9-9 in FIG. 8.

As shown best in FIGS. 8 and 9, an internal inflation lumen (310) extends longitudinally through guidewire shaft (302) along the central longitudinal axis of shaft (302). A proximal end of inflation lumen (310) fluidly communicates with an inflation medium source (not shown). A distal end of inflation lumen (310) fluidly communicates with an interior of balloon (308) via a plurality of apertures (312) that extend laterally through the sidewall of guidewire shaft (302). While guidewire shaft (302) of the present example includes four apertures (312) approximately aligned with a medial portion of balloon (308), any suitable quantity and arrangement of apertures (312) may be provided in other examples. As seen in FIG. 8, inflation lumen (310) terminates at a distal wall (314) located distal to the distal-most aperture (312) and proximal to a distal end of balloon (308). Inflation lumen (310) is configured to communicate a pressurized medium (e.g., saline) to and from the interior of balloon (308) in response to user input to enable selective inflation and deflation during a dilation procedure, for example as described below in connection with FIGS. 11A-11C.

Though not shown, guidewire (300) may be actuated with an actuating device of any suitable type that may be held and operated by a user, and which may have features similar to those disclosed in U.S. patent application Ser. No. 15/840,346, entitled "Dilation Instrument with Proximally Located Force Sensor," filed Dec. 13, 2017, published as U.S. Pub. No. 2019/0175887 on Jun. 13, 2019, the disclosure of which is incorporated by reference herein.

As shown best in FIGS. 7 and 8, guidewire (300) of the present example further includes a navigation sensor (316) (shown schematically) arranged at distal end (304) proximal to distal tip (306) and distal to the distal end of balloon (308). Navigation sensor (316) is operable to generate signals corresponding to the location of distal end (304) within a patient during a surgical procedure, and thus enables a surgeon to track the location of distal end (304) within the patient in real time, as described in greater detail below. Navigation sensor (316) may be in the form of an electrically conductive coil configured to generate an electrical signal when placed within an externally generated magnetic field, as described below.

As shown in FIGS. 8 and 9, guidewire (300) houses a pair of sensor wires (318) that couple to navigation sensor (316) and extend proximally through distal lumen wall (314) and inflation lumen (310) toward a proximal end of guidewire (300). The location at which sensor wires (318) extend through distal lumen wall (314) may be sealed with an adhesive (320) or other material suitable to prevent ingress of inflation fluid from lumen (310) toward navigation sensor (316). Accordingly, navigation sensor (316) is fluidically isolated from inflation lumen (310). Sensor wires (318) are configured to communicate electrical signals from navigation sensor (316) to the processor of a navigation system, such as processor (408) of surgical navigation system (400) described below. While only one navigation sensor (316) is shown, two or more navigation sensors may be provided in other examples at various locations within guidewire (300), for instance to track both a location and a rotational orientation of distal end (304) of guidewire (300) within the patient. It will be appreciated, however, that navigation sensor (316) is merely optional and may be entirely omitted from guidewire (300) in some examples. In such examples, guidewire (300) may be navigated through the anatomical passages of a patient with the assistance of various other suitable guidance devices and methods readily apparent to those skilled in the art, or without any such guidance devices.

B. Exemplary Surgical Navigation System Incorporating Guidewire

Image-guided surgery (IGS) is a technique in which a computer is used to obtain a real-time correlation of the location of an instrument that has been inserted into a patient's body to a set of preoperatively obtained images. In some IGS procedures, a digital tomographic scan (e.g., CT or MRI, 3-D map, etc.) of the operative field is obtained prior to surgery and converted into a digital map. Instruments having sensors mounted thereon are used to perform a surgical procedure while the sensors send data to the computer indicating the current position of each surgical instrument. The computer correlates the data it receives from the instrument-mounted sensors with the digital map. The tomographic scan images are displayed on a system display device (e.g., a video monitor) along with an indicator (e.g., cross hairs or an illuminated dot, etc.) showing the real-time position of each surgical instrument relative to the anatomical features shown in the scan images.

Figure 10:
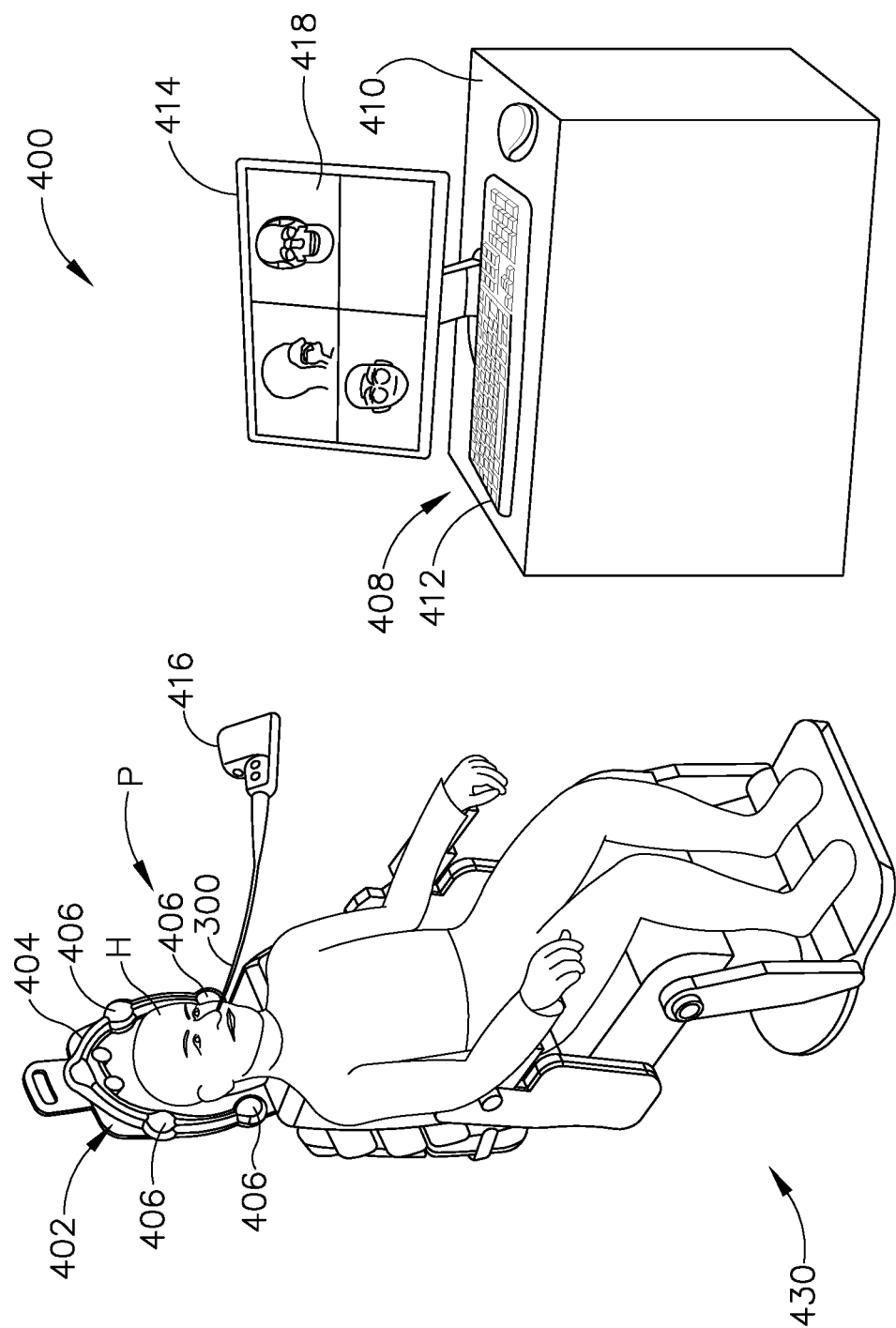
FIG. 10 depicts a schematic perspective view of an exemplary surgical navigation system that incorporates the guidewire of FIG. 7.

FIG. 10 shows an exemplary IGS navigation system (400) that incorporates guidewire (300) described above. Surgical navigation system (400) is configured to implement navigation sensor (316) of guidewire (300) to provide real-time location tracking of distal end (304) of guidewire (300) within a patient (P) during a surgical procedure. Surgical navigation system (400) includes a field generator assembly (402), which comprises a set of magnetic field generators (406) that are supported by a U-shaped frame (404) configured to be positioned about the head (H) of patient (P). Field generators (406) are operable to generate alternating magnetic fields of different frequencies around the patient's head (H). In the present example, frame (404) is mounted to the headrest of a chair (430), with patient (P) being seated in chair (430) such that frame (404) partially surrounds the patient's head (H). By way of example only, chair (430) and/or field generator assembly (102) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein.

Navigation sensor (316) is provided in the form of one or more electrically conductive coils in the present example. The presence of navigation sensor (316) in the alternating magnetic generated by field generators (406) field induces an electrical current in sensor (316), which is communicated as an electric signal proximally through sensor wires (318) to a processor (408) of surgical navigation system (400). Processor (408) receives the signals and executes an algorithm to determine a location of navigation sensor (316) within a three-dimensional space occupied by the alternating electromagnetic field, which surrounds head (H) of patient (P) in the present example. Processor (408) correlates this three-dimensional space to the known anatomy of patient (P), analyzed preoperatively, and determines the three-dimensional location of sensor (316) with patient (P).

Processor (408) of surgical navigation system (400) comprises a processing unit that communicates with one or more memories and is configured to control field generators (406) and other elements of navigation system (400). In the present example, processor (408) is mounted in a console (410), which comprises operating controls (412) that include a keypad and/or a pointing device such as a mouse or trackball. A physician uses operating controls (412) to interact with processor (408) while performing the surgical procedure. Processor (408) uses software stored in a memory of processor (408) to calibrate and operate system (400). Such operation includes driving field generators (406), processing data received from navigation sensor (316), processing data from operating controls (412), and driving a display (414).

Guidewire navigation sensor (316) of the present example communicates with system processor (408) via a communication unit (416) that is coupled with a proximal end of guidewire (300), as shown schematically in FIG. 10, and connects with the proximal ends of sensor wires (318). Communication unit (416) is configured to provide wireless communication of data and other signals between console (410) and navigation sensor (316). Alternatively, some other versions may provide wired coupling between communication unit (416) and console (410).

System display (414) is operable to depict a navigation image (418) that shows the real-time position of distal end (304) of guidewire (300) in relation to anatomy of patient (P). The anatomy may be presented by navigation image (418) in the form of a video camera image, a CT scan image, and/or a computer generated three-dimensional model of the anatomy, which may be displayed simultaneously and/or superimposed on each other, for instance. In addition to the anatomy image, navigation image (418) shows a graphical representation of guidewire (300). This graphical representation is superimposed on the anatomy image and enables the physician to identify the position of distal end (304) of guidewire (300) relative to adjacent anatomical features of patient (P) in real-time during a surgical procedure. By way of example only, display (414) may depict navigation image (418) in accordance with at least some of the teachings of U.S. Pat. Pub. No. 2016/0008083, issued as U.S. Pat. No. 10,463,242 on Nov. 5, 2019, entitled "Guidewire Navigation for Sinuplasty," incorporated by reference above.

The IGS components of surgical navigation system (400) may be further configured in accordance with one or more teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; U.S. Pat. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

C. Exemplary Method of Dilating Eustachian Tube Using Guidewire

FIGS. 11A-12C show an exemplary method of dilating the ET (26) of a patient using guidewire (300) described above. Rather than inserting guidewire (300) through a nostril, into the nasal cavity, and through the pharyngeal ostium (28), the method shown in FIGS. 11A-12C includes accessing the ET (26) through the ear canal (20) and the tympanic membrane (22). In the present example, guidewire (300) is advanced through ear canal (20) and navigated through the internal passageways of the patient's head with real-time guidance provided by navigation sensor (316) and IGS navigation system (400) as described above. As also described above, however, navigation sensor (316) is merely optional. Accordingly, in other examples, guidewire (300) may be employed to access and dilate the ET (26) with alternative types of guidance features, such as an endoscope or an illuminating fiber (not shown); or without any such guidance features.

Those of ordinary skill in the art will recognize that the tympanic membrane (22) provides a physical barrier to passage of an instrument such as balloon catheter (400) from the ear canal (20) into the ET (26). Thus, an operator must somehow address the presence of the tympanic membrane (22) in order to gain access to the ET (26) from the ear canal (20). The following description provides a merely illustrative method for handling the tympanic membrane (22) in order to suitably insert guidewire (300) into the ET (26) via the ear canal (20). Other illustrative methods are disclosed in U.S. Pat. Pub. No. 2017/0119583, entitled "System and Method for Treatment of Eustachian Tube from Middle Ear Approach," published on May 4, 2017, issued as U.S. Pat. No. 10,070,993 on Sep. 11, 2018, the disclose of which is incorporated by reference herein.

In the example shown in FIGS. 11A-12C, the operator accesses the middle ear (14) and ET (26) without compromising the integrity of the tympanic membrane (22). As shown in FIG. 12A, the operator makes an incision along line (502) in the tissue surrounding tympanic membrane (22) but does not cut any part of tympanic membrane (22) itself. In the present example, cut line (502) is made adjacent to an inferior aspect of the tympanic membrane (22), along approximately half the perimeter of the tympanic membrane (22). Cut line (502) may be formed using any suitable conventional instrumentation. In other variations, cut line (502) may be made such that it extends along a different portion of the tympanic membrane (22) and may include a different length or shape than that shown. Other suitable positioning and configurations of cut line (502) that may be made in order to create a sufficient opening (504) for access to the middle ear (14) and ET (26) will be apparent to persons skilled in the art in view of the teachings herein. As shown in FIGS. 11A-11B and 12B, cut line (502) forms a flap (506) that may be folded superiorly such that an opening (504) is created that provides access to the middle ear (14) and ET (26). Alternatively, flap (506) may be folded in a different manner or direction in order to create an opening with access to the middle ear (14) and ET (26).

As shown in FIG. 12B, the operator fixes flap (506) to a superior portion of the ear canal (20) using a suture (508). To protect the integrity of the tympanic membrane (22), the operator does not puncture or otherwise compromise the tympanic membrane (22) with a needle when implanting suture (508) on flap (506). In some other examples, the operator may affix the flap (506) in a folded configuration in a different manner, such as by adhesive, or in any other suitable manner as will be apparent to persons skilled in the art in view of the teachings herein.

As shown in FIG. 11A, once a sufficient opening (504) is created, the operator may direct a distal end portion of guidewire (300) into the ear canal (20), through opening (504), through the middle ear (14), past the isthmus (29), and into the ET (26). Throughout insertion into the ET (26), balloon (308) is in its deflated state in which it provides guidewire (300) with a maximum outer diameter of approximately 1 millimeter or less as described above, to thereby minimize disruption to isthmus (29) and adjacent components of inner ear (16). As described above, guidewire shaft (302) is formed with a suitably rigid construction such that guidewire (300) may be advanced through the internal passages of the patient without an external guidance device and without buckling.

Figure 11B:
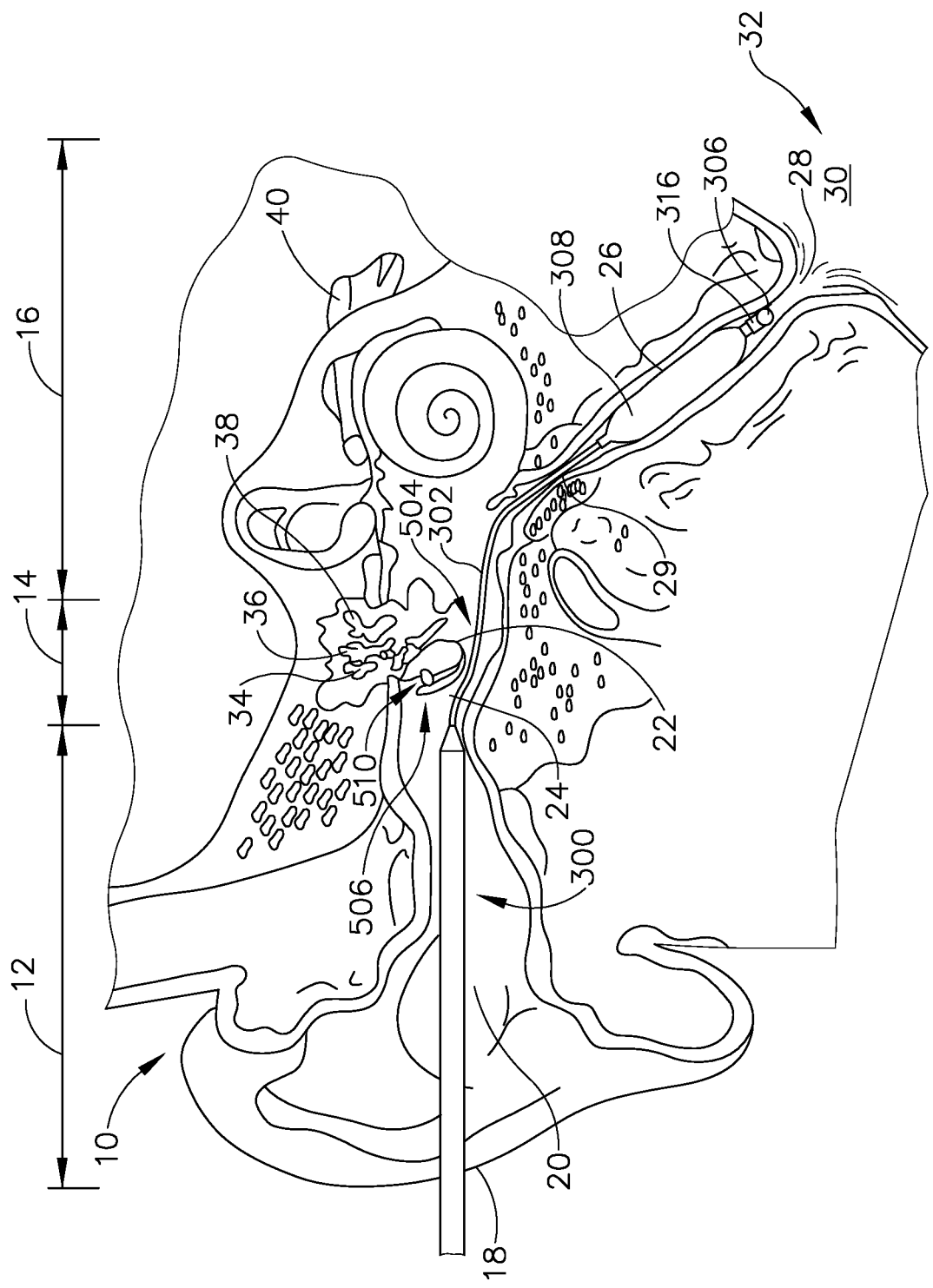
FIG. 11B depicts a cross-sectional view of the patient's head of FIG. 11A, showing the balloon of the guidewire inflated to thereby dilate the Eustachian tube.

As shown in FIG. 11B, once balloon (308) is suitably positioned within the ET (26), the operator inflates balloon (308) to thereby dilate the ET (26). As described above, balloon (308) may be configured to provide guidewire (300) with a maximum outer diameter of approximately 6 millimeters or more when inflated to provide a desired degree of ET dilation. Once inflated, balloon (308) may then be held in place within the ET (26) for an extended period of time (e.g. several seconds or minutes). In some instances, the operator may wish to repeatedly inflate and deflate balloon (308) within the ET (26) to achieve a desired dilation effect. Additionally, in some examples balloon (308) may be configured to carry an expandable stent for delivery into the ET (26) upon expansion of balloon (308). Once the ET (26) has been suitably dilated, balloon (308) may be guidewire (300) may be withdrawn from the ET (26) by reversing the insertion steps described above.

Following removal of balloon guidewire (300), the ET (26) is left dilated and able to resume normal functioning. Also following removal of guidewire (300) from the patient, the operator may replace flap (506) as generally shown in FIG. 12C. In the present example, the operator severs, decouples, or otherwise removes suture (508) and causes flap (506) to return to the inferior position adjacent to cut line (502). Then, the operator couples the flap (506) with the tissue adjacent to cut line (502), for example with an adhesive. Suitable surgical adhesives will be apparent to persons skilled in the art in view of the teachings herein. In other examples, the operator may couple the flap (506) to the tissue adjacent to cut line (502) in some other fashion, such as via suturing. Other suitable techniques that may be used to couple the flap (506) to the tissue adjacent to cut line (502) will be apparent to persons skilled in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A guidewire comprising: (a) a guidewire shaft, wherein at least a portion of the guidewire shaft is comprised of metal, wherein the guidewire shaft includes a lumen; and (b) an inflatable element arranged at a distal end of the guidewire shaft, wherein an interior of the inflatable element fluidly communicates with the lumen, wherein the inflatable element is operable to transition between a deflated state in which the inflatable element is configured to pass through an isthmus of a Eustachian tube (ET), and an inflated state in which the inflatable element is configured to dilate the ET.

EXAMPLE 2

The guidewire of Example 1, wherein at least a portion of the guidewire shaft is comprised of braided stainless steel.

EXAMPLE 3

The guidewire of any of the previous Examples, wherein the lumen extends along a central axis of the guidewire shaft.

EXAMPLE 4

The guidewire of any of the previous Examples, further comprising a closed distal tip.

EXAMPLE 5

The guidewire of any of Example 4, wherein the closed distal tip is sized and configured to pass through the isthmus of the ET.

EXAMPLE 6

The guidewire of any of the previous Examples, wherein the inflatable element comprises a balloon.

EXAMPLE 7

The guidewire of any of the previous Examples, wherein the guidewire is configured to assume a maximum outer diameter of 1 millimeter or less when the inflatable element is in the deflated state.

EXAMPLE 8

The guidewire of any of the previous Examples, wherein the inflatable element is configured to provide the guidewire with a maximum outer diameter of at least 6 millimeters when the inflatable element is in the inflated state.

EXAMPLE 9

The guidewire of any of the previous Examples, further comprising a navigation sensor operable to generate a signal corresponding to a location of a distal end of the guidewire within a patient.

EXAMPLE 10

The guidewire of Example 9, wherein the navigation sensor comprises an electromagnetic sensor.

EXAMPLE 11

The guidewire of any of Examples 9 through 10, wherein the electromagnetic sensor comprises an electrically conductive coil.

EXAMPLE 12

The guidewire of any of Examples 9 through 11, wherein the navigation sensor is arranged distal to the inflatable element.

EXAMPLE 13

The guidewire of any Examples 9 through 12, wherein the navigation sensor is isolated from the lumen.

EXAMPLE 14

The guidewire of any of Examples 9 through 13, wherein the lumen terminates at a distal wall, wherein the navigation sensor is located distal to the distal wall, wherein the guidewire further comprises a sensor wire that extends through the lumen and the distal wall and is coupled to the navigation sensor, wherein the sensor wire is configured to communicate the signal generated by the navigation sensor.

EXAMPLE 15

A surgical navigation system comprising: (a) the guidewire of any of Examples 9 through 14; and (b) a processor in communication with the navigation sensor, wherein the processor is operable to receive and analyze the signal generated by the navigation sensor to determine the location of the distal end of the guidewire within the patient.

EXAMPLE 16

A guidewire comprising: (a) a guidewire shaft, wherein the guidewire shaft includes a lumen; (b) an inflatable element arranged at a distal portion of the guidewire shaft, wherein an interior of the inflatable element fluidly communicates with the lumen, wherein the inflatable element is operable to transition between a deflated state in which the inflatable element is configured to pass through an isthmus of a Eustachian tube (ET), and an inflated state in which the inflatable element is configured to dilate the ET; and (c) a navigation sensor, wherein the navigation sensor is operable to generate a signal corresponding to a location of a distal end of the guidewire within a patient.

EXAMPLE 17

The guidewire of Example 16, wherein the navigation sensor comprises an electrically conductive coil.

EXAMPLE 18

The guidewire of any of Examples 16 through 17, wherein the navigation sensor is arranged distal to a proximal end of the inflatable element.

EXAMPLE 19

A guidewire comprising: (a) a guidewire shaft, wherein at least a portion of the guidewire shaft is comprised of metal; and (b) an expandable element arranged at a distal portion of the guidewire shaft, wherein the expandable element is operable to transition between an unexpanded state in which the expandable element is configured to pass through an isthmus of a Eustachian tube (ET), and an expanded state in which the expandable element is configured to dilate the ET, wherein the guidewire is configured to assume a maximum outer diameter of 1 millimeter or less when the expandable element is in the unexpanded state.

EXAMPLE 20

The guidewire of Example 19, wherein the expandable element is configured to provide the guidewire with a maximum outer diameter of at least 6 millimeters when the expandable element is in the expanded state.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A guidewire comprising:
   (a) a guidewire shaft, wherein at least a portion of the guidewire shaft is comprised of metal, wherein the guidewire shaft includes a lumen;
   (b) a non-compliant balloon arranged at a distal end of the guidewire shaft, wherein an interior of the non-compliant balloon fluidly communicates with the lumen, wherein the non-compliant balloon is operable to transition between a deflated state in which the non-compliant balloon is configured to pass through an isthmus of a Eustachian tube (ET), and an inflated state in which the non-compliant balloon is configured to dilate the ET, wherein the guidewire is configured to assume a maximum outer diameter of 1 millimeter or less when the non-compliant balloon is in the deflated state, wherein the non-compliant balloon has a maximum outer diameter of at least 6 millimeters when the non-compliant balloon is in the inflated state to dilate the ET;
   (c) a navigation sensor operable to generate a signal corresponding to a location of a distal end of the guidewire within a patient; and
   (d) a sensor wire operatively coupled with the navigation sensor, wherein the sensor wire is fixably attached to an inner surface of the guidewire shaft within the inflatable element.

2. The guidewire of claim 1, wherein at least a portion of the guidewire shaft is comprised of braided stainless steel.

3. The guidewire of claim 1, wherein the lumen extends along a central axis of the guidewire shaft.

4. The guidewire of claim 1, wherein the navigation sensor comprises an electromagnetic sensor.

5. The guidewire of claim 4, wherein the electromagnetic sensor comprises an electrically conductive coil.

6. The guidewire of claim 1, wherein the navigation sensor is arranged distal to the non-compliant balloon.

7. The guidewire of claim 1, wherein the navigation sensor is isolated from the lumen.

8. The guidewire of claim 1, wherein the lumen terminates at a distal wall, wherein the navigation sensor is located distal to the distal wall, wherein the sensor wire extends through the lumen and the distal wall and is coupled to the navigation sensor, wherein the sensor wire is configured to communicate the signal generated by the navigation sensor.

9. The guidewire of claim 1, wherein the elongate shaft includes a plurality of apertures that are configured to fluidly communicate the lumen with the interior of non-compliant balloon, wherein the apertures are aligned with a medial portion of the non-compliant balloon.

10. The guidewire of claim 1, wherein the ratio of the maximum outer diameter in the inflated state relative to the maximum outer diameter in the deflated state is at least 6:1.

11. A surgical navigation system comprising:
    (a) the guidewire of claim 1; and
    (b) a processor in communication with the navigation sensor, wherein the processor is operable to receive and analyze the signal generated by the navigation sensor to determine the location of the distal end of the guidewire within the patient.

12. A guidewire comprising:
    (a) a guidewire shaft that defines a longitudinal axis, wherein the guidewire shaft includes a lumen;

(b) an inflatable element arranged at a distal portion of the guidewire shaft, wherein an interior of the inflatable element fluidly communicates with the lumen, wherein the inflatable element is operable to transition between a deflated state in which the inflatable element is configured to pass through an isthmus of a Eustachian tube (ET), and an inflated state in which the inflatable element is configured to dilate the ET;

(c) a navigation sensor, wherein the navigation sensor is operable to generate a signal corresponding to a location of a distal end of the guidewire within a patient; and (d) a sensor wire that extends along the longitudinal axis through the entire inflatable element, wherein the sensor wire is fixably attached with an inner surface of the guidewire shaft within the inflatable element.

13. The guidewire of claim 12, wherein the navigation sensor comprises an electrically conductive coil.

14. The guidewire of claim 12, wherein the navigation sensor is arranged distal to a proximal end of the inflatable element.

15. The guidewire of claim 12, wherein the inflatable element includes a non-compliant balloon, wherein the guidewire is configured to assume a maximum outer diameter of 1 millimeter or less when the non-compliant balloon is in the deflated state, wherein the non-compliant balloon is configured to provide the guidewire with a maximum outer diameter of at least 6 millimeters when the non-compliant balloon is in the inflated state.

16. The guidewire of claim 15, wherein the ratio of the maximum outer diameter in the inflated state relative to the maximum outer diameter in the deflated state is at least 6:1.

17. The guidewire of claim 12, wherein the lumen terminates at a distal wall, wherein the navigation sensor is located distal to the distal wall, wherein the sensor wire that extends through the lumen and the distal wall and is coupled to the navigation sensor, wherein the sensor wire is configured to communicate the signal generated by the navigation sensor.

18. The guidewire of claim 12, wherein the sensor wire is fixably attached to the inner surface of the guidewire shaft using an adhesive.

19. A guidewire comprising:

(a) a guidewire shaft, wherein at least a portion of the guidewire shaft is comprised of metal;

(b) a non-compliant balloon arranged at a distal portion of the guidewire shaft, wherein the non-compliant balloon is operable to transition between an unexpanded state in which the non-compliant balloon is configured to pass through an isthmus of a Eustachian tube (ET), and an expanded state in which the non-compliant balloon is configured to dilate the ET, wherein the guidewire is configured to assume a maximum outer diameter of 1 millimeter or less when the non-compliant balloon is in the unexpanded state, wherein the non-compliant balloon has a maximum outer diameter of at least 6 millimeters when the non-compliant balloon is in the expanded state to dilate the ET, wherein the ratio of the maximum outer diameter in the expanded state relative to the maximum outer diameter in the unexpanded state is at least 6:1;

(c) a navigation sensor operable to generate a signal corresponding to a location of a distal end of the guidewire within a patient; and (d) a sensor wire operatively coupled with the navigation sensor, wherein the sensor wire is fixably attached to an inner surface of the guidewire shaft within the inflatable element.

20. The guidewire of claim 19, wherein the non-compliant balloon has a working length of approximately 12 millimeters to approximately 24 millimeters.

\* \* \* \* \*